United States Patent [19]

Terzian et al.

[11] Patent Number: 5,198,173
[45] Date of Patent: Mar. 30, 1993

[54] PROCESS FOR PREPARING ADVANCED COMPOSITE STRUCTURES

[75] Inventors: ALbert Terzian, Ridley Park, Pa.; Joseph D. Trentacosta, Wilmington, Del.

[73] Assignee: E. I. Du Pont de Nemours and Company, Wilmington, Del.

[21] Appl. No.: 626,886

[22] Filed: Dec. 13, 1990

[51] Int. Cl.$^5$ ............................................. B29C 45/16
[52] U.S. Cl. .................................... 264/257; 264/510
[58] Field of Search ............... 264/255, 261, 257, 258, 264/510

[56] References Cited

U.S. PATENT DOCUMENTS

| | | |
|---|---|---|
| 4,013,748 | 3/1977 | Valyi . |
| 4,164,794 | 8/1979 | Spector et al. . |
| 4,268,468 | 5/1981 | Esper et al. . |
| 4,351,069 | 9/1982 | Ballintyn et al. . |
| 4,606,395 | 8/1986 | Ban . |
| 4,615,855 | 10/1986 | Orlowski et al. . |
| 4,634,563 | 1/1987 | Hancock . |
| 4,637,909 | 1/1987 | Lucca . |
| 4,662,887 | 5/1987 | Turner et al. . |
| 4,681,718 | 7/1987 | Oldham . |
| 4,750,905 | 6/1988 | Koeneman et al. . |
| 4,769,197 | 9/1988 | Kromrey . |
| 4,770,835 | 9/1988 | Kromrey . |
| 4,837,251 | 6/1989 | Okey et al. . |
| 4,842,787 | 6/1989 | Chess et al. . |
| 4,892,552 | 1/1990 | Ainsworth et al. . |

FOREIGN PATENT DOCUMENTS

| | | |
|---|---|---|
| 176640 | 4/1986 | European Pat. Off. . |
| 320302 | 6/1986 | European Pat. Off. . |
| 195561 | 9/1986 | European Pat. Off. . |
| 197441 | 10/1986 | European Pat. Off. . |
| 277727 | 8/1988 | European Pat. Off. . |
| 357301 | 3/1990 | European Pat. Off. . |
| 2555902 | 6/1985 | France . |
| 85/04323 | 10/1985 | PCT Int'l Appl. . |

OTHER PUBLICATIONS

Egerton et al., Proceedings of the 33rd International SAMPE Symposium, 1988, pp. 35-46.

Primary Examiner—Tim Heitbrink
Attorney, Agent, or Firm—William H. Hamby

[57] ABSTRACT

A novel procedure for molding composite structures is disclosed wherein the finished part exhibits a net shape geometry requiring minimal further machining and displaying enhanced consolidation and surface characteristics. A composite preform having a hollow core portion containing a polymer insert is introduced into a mold cavity. One end of the preform core is sealed and the preform together with the polymer insert is heated to melt the composite matrix and core polymer. Pressure is applied to the core at the other end of the part, causing radial expansion of the part against the molded cavity and consolidation of the composite into a finished part. A product finished part is also disclosed and is useful as a component of an orthopedic implant.

16 Claims, 7 Drawing Sheets

PROCESS FOR PREPARING ADVANCED COMPOSITE STRUCTURES

FIELD OF THE INVENTION

The present invention relates to a process for molding advanced composite structures. More particularly, the present invention relates to molding processes that enhance the consolidation and surface of such composite structures including those used as orthopedic implants and to the products thereof.

BACKGROUND OF THE INVENTION

Advanced fiber reinforced, organic matrix, composite materials provide designers of high performance structures with significant advantages in strength-to-weight and stiffness-to-weight as well as resistance to environmental corrosion when compared to metals. Also, in several applications, including load bearing medical implants, the ability to adjust the modulus of elasticity of a composite by varying fiber orientation, concentration and type is used to great advantage in achieving optimal load distribution in comparison with metallic structures characterized by a single, uniform modulus of elasticity. Such metallic structures are characterized by high, fixed moduli of elasticity which makes it difficult to achieve optimal device stiffness within a given anatomical geometric envelope.

Both thermoset and thermoplastic polymers have found application as the matrix in these composite systems. Thermoplastic composites have received increasing attention in recent years because of their greater fracture toughness when compared to thermoset systems. In addition, thermoplastics offer the advantages of thermal processing instead of the reactive cure processing characteristic of thermosets.

However, fabrication of thermoplastic matrix composite structures, especially those of complex shape, offers considerable challenge. Although flow of the fully polymerized matrix resin occurs with the application of heat and pressure, thermoplastic melts are usually characterized by high viscosities often several orders of magnitude higher than uncured thermosets. Impregnation of the reinforcement fiber bundles is, therefore, difficult and consolidation of the resultant structure to eliminate residual voids, which can be deleterious to mechanical performance, is often incomplete. Well known impregnation and consolidation processes effectively used with thermosets, including resin transfer molding, are usually ineffective with thermoplastics.

One process for fabricating thermoplastic matrix composite systems which is capable of high consolidation is compression molding. Lamina of preimpregnated composite material are layed up at the desired fiber orientation and placed in a closed mold and subjected to heat and pressure to produce a well consolidated mass. Alternatively, alternating layers of fiber and matrix film or comingled bundles of reinforcing fiber and matrix fiber may be used in place of the preimpregnated lamina. In anycase, this process is largely limited to the production of structures of simple shape; specifically, flat or simply curved shapes. Besides the limitation in shape, these parts are often characterized by the appearance of cut fiber ends on four sides which can lead to delamination in service. The formation of a complex shape, such as an orthopedic implant, from such a compression molded mass requires additional machining operations which lead to further exposure of additional free fiber ends.

U.S. Pat. No. 4,892,552 describes production of a composite orthopedic device by machining a composite block itself fabricated by compression molding. European Patent Publication 0 277 727 also describes production of a composite orthopedic device from a block fabricated by compression molding. Prostheses of this reference are formed from plies of continuous filament fibers which are stacked and compression molded. In the latter case the molded block is simply curved but fiber ends are still exposed at the edges. Furthermore, the finished devices are obtained only by additional machining and the like. Articles produced according to the present invention may be formed as finished parts within the mold itself.

More preferred approaches to the production of composite structures with significant curvature and/or complex shape include nearer net shape fiber placement processes such as filament winding and braiding. These processes are capable of producing parts comprising closed contours, thus, minimizing free fiber ends and potential sites of delamination. In addition, these processes are compatible with the incorporation of varying fiber orientation within a structure so that local stiffness and strength can be tailored to the mechanical requirements of the application. Furthermore, these processes are easily mechanized and computerized making them suitable for production at high efficiency and low cost.

In situ consolidation of thermoplastic composites has been demonstrated during filament winding and braiding by application of heat and fiber tension during the placement of reinforcing tow preimpregnated with matrix. See for example, M. W. Egerton and M. B. Gruber, "Thermoplastic Filament Winding Demonstrating Economies and Properties Via In-Situ Consolidation", Proceedings of the 33rd International SAMPE Symposium, 1988, pp. 35–46. Nevertheless, experience with such processes suggests that further consolidation is often desirable. Even if complete fusion occurs at the interface between the composite tow and the previously wound or braided mass, voids may still be present in the structure as a result of incomplete consolidation in the earlier tow manufacturing process. In addition, voids may remain in the as-wound or as-braided part as a result of upsets in the winding or braiding process including tow breaks. Further consolidation may also be desirable to improve the surface characteristics of the structure. As-wound or as-braided parts are typically characterized by uncontrolled surface topology which may be deleterious in service. For example, a surface of precise dimension may be required to enable joining the structure to an adjacent part or a surface of precise contour and smoothness may be required to achieve acceptable aerodynamic performance in aircraft applications.

In general, further consolidation of filament wound or braided structures cannot be achieved by conventional compression or autoclave molding. Attempts to apply pressure to the outside of a contoured as-wound or braided structure can result in collapse of the composite if the structure has a hollow core. If the core is filled, for example by a rigid mandrel, conventional compression or autoclave molding will still result in severe distortion of the composite as the fiber bundles buckle under the resultant compressive stresses.

A more preferred approach to consolidation of near net shape filament wound or braided structures involves applying pressure to the core of the structure and allowing the composite mass to expand against a rigid mold whose cavity follows the contours of the desired finished shape and has acceptable surface smoothness. In this way, the reinforcing fibers comprising the composite are subjected to a tensile rather than a compressive stress and no distortion occurs. Having been wound or braided over a mandrel which is removed, the as-wound or as-braided structure usually has a hollow core within which the consolidating pressure can be applied. Various approaches to the application of pressure in the core of structure have been reported. In one approach, an elastomeric bladder is installed in the core of the composite and the bladder is pressurized with a gas. In another approach a material of high coefficient of thermal expansion (CTE) is placed in the core. As the system is heated to a temperature at which the composite matrix becomes fluid, the high CTE material expands to a greater extent than the surrounding composite and, thus, forces the composite against the mold surface.

In both approaches to internal pressurization described above, a foreign material, comprising the bladder or high CTE material, is used. This places a significant limitation on the applicability of these processes since these materials must have acceptable performance at a very high temperature equal to that at which the composite matrix is fluid and has acceptably low viscosity. For many matrix materials, for example, polyetheretherketones, this process temperature can be 400° C. In addition, this foreign material may infiltrate the composite structure with consequent deleterious effects. In medical implant systems, for example, the infiltration of a foreign material may compromise the otherwise biocompatible nature of the composite system.

It is an object of the present invention to provide a method of molding thermoplastic matrix, fiber reinforced composite structures to achieve a net shape geometry with enhanced consolidation and without temperature limitation and without the necessity to introduce a foreign material It is a further object of the present invention to provide a method of preparing composite orthopedic devices exhibiting minimal void formation and precise surface shape and smoothness. A feature of the process of the present invention is the adaptability of the molding process with other processing techniques. An advantage of the process described herein is the production of structures having tight tolerances to accommodate specific geometric envelopes. These and other objects, features and advantages will become apparent upon having reference to the following description of the invention.

SUMMARY OF THE INVENTION

A method of making a composite structure is disclosed comprising several steps. First, a composite preform is provided for disposition within a mold cavity. The preform has a hollow core portion and an external configuration which is undersized relative to the cavity of the mold.

The preform is introduced into the cavity which has an internal configuration appropriate to the configuration of a finished part. That is, the cavity follows the contours of the finished part. One or more openings to the core of the preform is plugged with one or more plugs to prevent polymer flow from these openings. Polymer is introduced into the core of the preform. The polymer may be the same as that comprising the composite matrix or it may be different. Heat is applied to the preform together with the polymer in the core so as to melt the polymer in the core. That is, the composite matrix and the core polymer are molten. Pressure is applied to the polymer in the core of the preform via one or more remaining, unplugged openings to the core of the preform to cause expansion of the preform against the internal configuration of the mold cavity and to consolidate the preform to form a finished part. The finished part is cooled while maintaining pressure on the core, and subsequently removed from the mold.

There is also disclosed articles of manufacture according to the above described process, including finished parts useful for orthopedic implants.

DETAILED DESCRIPTION OF THE INVENTION

Figure 1:
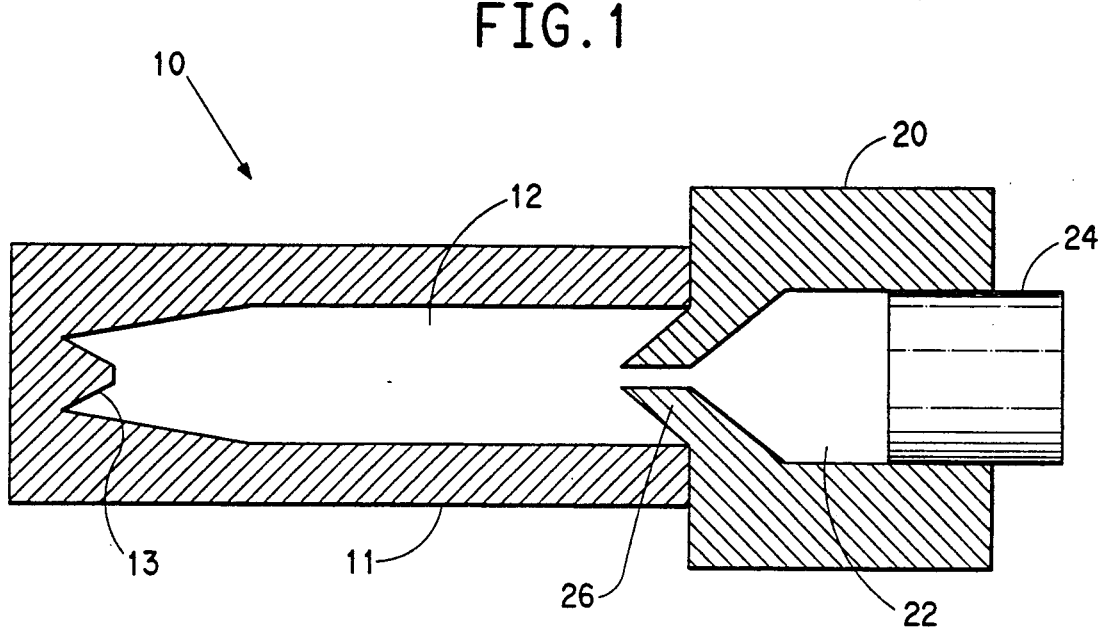
FIG. 1 is a cross-sectional view of a net shape molding system according to the present invention.
Figure 2A:
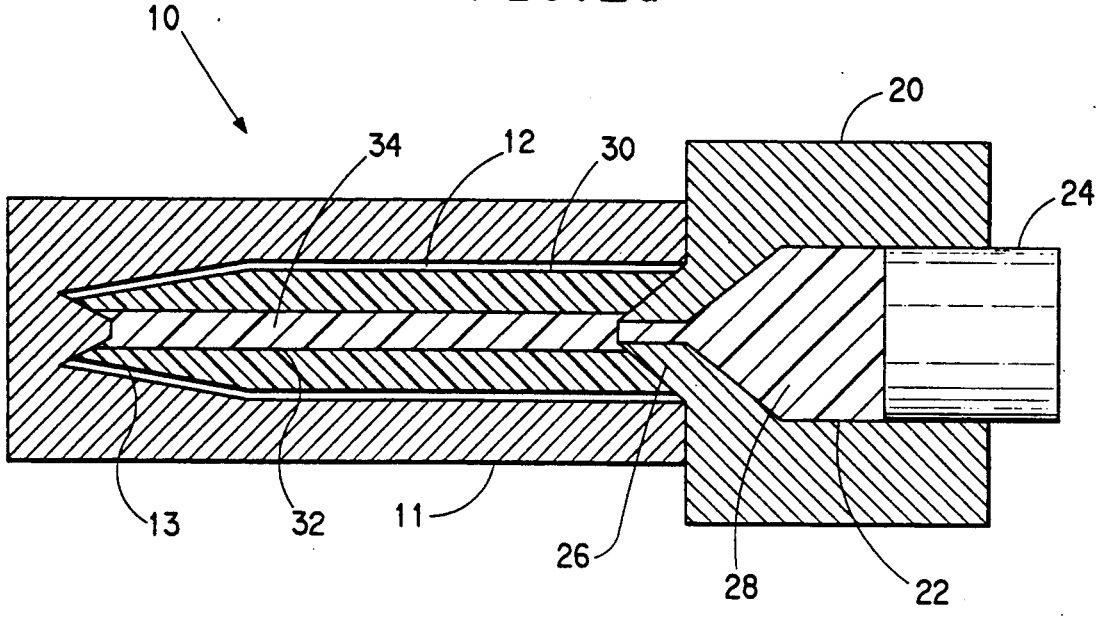
FIG. 2a is a cross-sectional view of a net shape molding system according to the present invention with a composite preform installed.

Having reference to FIG. 1, the net shape molding system is disclosed generally at 10. The mold body 11 has a mold cavity 12 which accommodates a preform. A reinforcing fiber tow preimpregnated with a thermoplastic polymer is transformed into the preform using a filament winder, such as those made by the McClean Anderson Co., or a braiding machine, such as those made by the Wardwell Co. More complex preforms may be made using fiber placement machines incorporating a robot such as that described in U.S. Pat. No. 4,750,960. In all cases these preform generating machines may incorporate means to apply heat and pressure to the preimpregnated tow so as to at least partially consolidate the preform. As seen in FIG. 2a, the core 32 of preform 30 is prefilled with polymer insert 34. One end of the core 32 of the preform 30 is plugged by end plug 13, the end of the core 32 having been previously shaped to form a close seal with plug 13. The other end of the core of the preform receives polymer outlet 26 of the structure 20, again the core having been previously shaped to form a close seal with outlet 26. Polymer reservoir 22 is also prefilled with polymer insert 28. Polymer inserts 34 and 28 may be the same polymer as that forming the matrix of composite preform 30 or they may be different. However, the polymer comprising these inserts must be molten and stable at a temperature at which the composite matrix is molten. The polymer and thermoplastic matrix are preferably independently selected from the group consisting of polyamide, polyester, polysulfone, polyether-ether-ketone, polyether-ketone-ketone, polyimide, copolymers of tetrafluoroethylene and perfluorovinylether and copolymers of polytetrafluoroethylene and ethylene. The inserts 34 and 28 may be produced in a separate step by various techniques including machining or injection molding.

The system is heated to an appropriate temperature at which the composite matrix is molten and of sufficiently low viscosity to enable consolidation but not so high as to enable rapid polymer degradation. A load is applied to piston 24 creating a pressure in polymer 28 which is transmitted to core polymer 34 via the aperture in outlet 26 and is further transmitted to the wound or braided preform which then moves radially against the mold surface. Polymer melt is transferred from the reservoir 22 (containing polymer in excess of that within the core 32 prior to pressurization and optionally shaped to facilitate the urging of polymer into the core) to the core 32 via the aperture in outlet 26 as needed to accomodate the volume change as the preform expands to the mold cavity dimensions. The system is held at the consolidation temperature and pressure long enough to insure the substantial elimination of voids in the finished part. The part is then cooled below the glass transition temperature of the matrix while maintaining pressure on the system. The entire assembly can be placed in a vacuum chamber to enhance gas removal. In order to facilitate part removal, the mold body may comprise multiple parts clamped or bolted together during processing but disassembled after cooling and depressurization. The mold may be heated by inserting electrical heaters into the mold body or by providing passages in the mold body through which a heated fluid is circulated. In addition, the same or other passages may be provided to circulate a cooling fluid.

Figure 3:
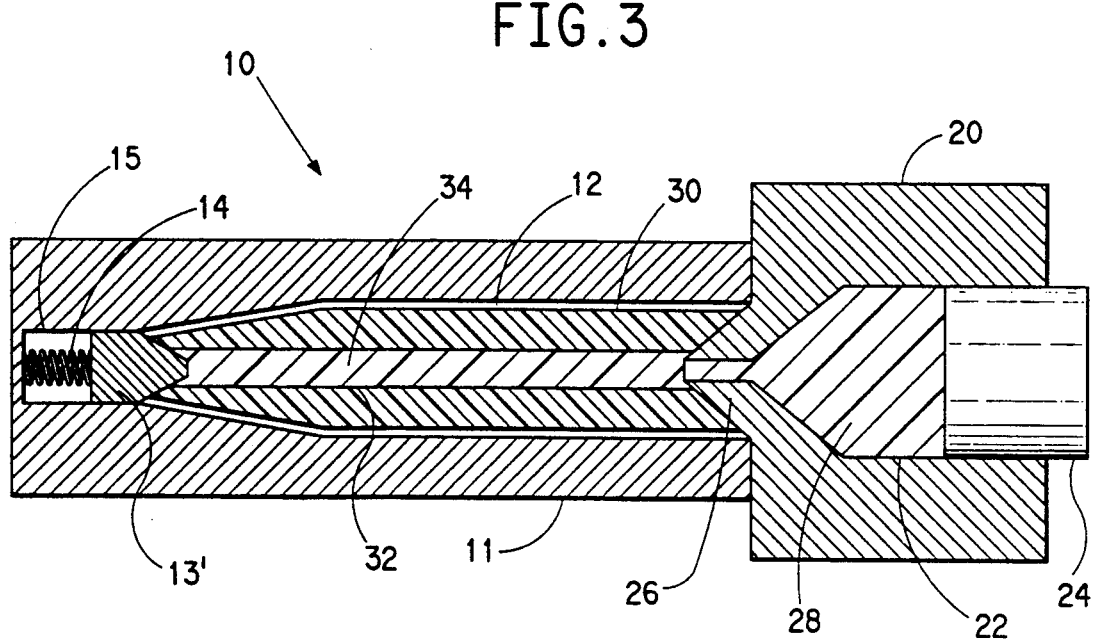
FIG. 3 is a cross-sectional view of a net shape molding system according to the present invention with means of sealing the core of the preform.

For many systems fixed plugs 13 are sufficient to prevent polymer flow from the plugged openings. However, for other material systems polymer leaks may develop around end plug 13 and polymer outlet 26, thus, reducing the effective pressurization of the core. Sealing may be enhanced by spring loading a movable end plug 13' as shown in FIG. 3. Spring 14 resides in cavity 15 in mold body 11 and bears against movable end plug 13' which, in turn, is received in core 32 of preform 30. At installation, spring 14 is compressed such that a preload is imposed on preform 30 along the axis of mold cavity 11. Then as the preform 30 is heated and pressurized any motion of preform 30 which would otherwise cause a leak is accomodated by the action of spring 14 which allows end plug 13' to move with preform 30, thus, maintaining a seal and impeding polymer leakage. The axial load imposed by spring 14 also maintains a seal at stationary outlet 26. Spring 14 may comprise, for example, an assembly of spring washers such as those called Belleville spring washers.

Figure 2B:
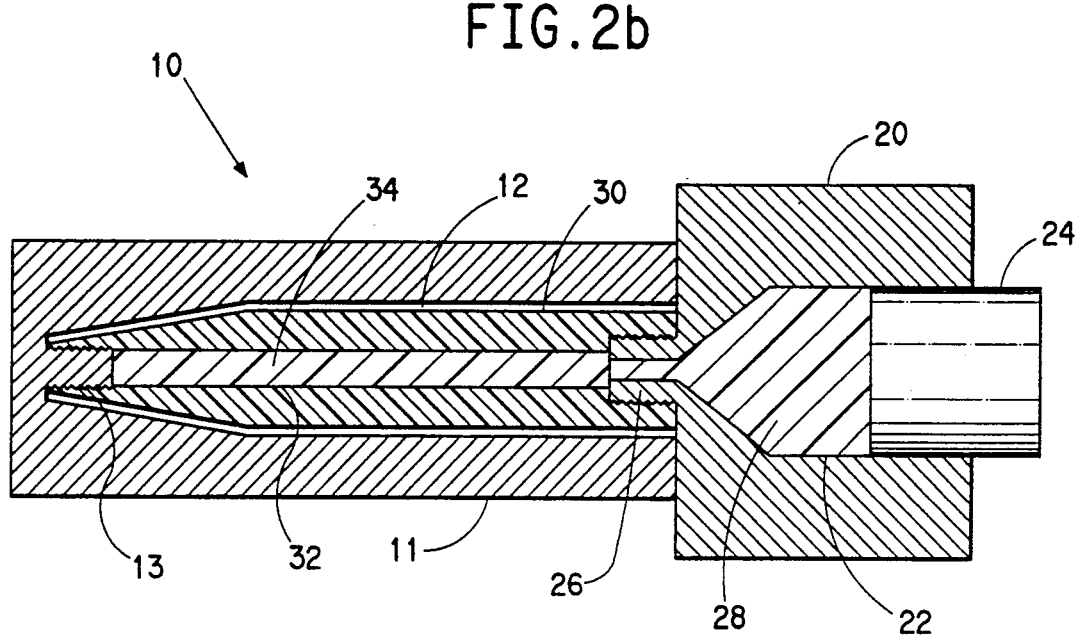
FIG. 2b is a cross-sectional view of a net shape molding system according to the present invention with a composite preform installed and a means of sealing the core of the preform.

Polymer leakage around plugs 13 and outlet 26 may be reduced by changing the shape of these features from the tapered geometry depicted in FIGS. 2a and 3 to a threaded shape as depicted in FIG. 2b. This threaded shape produces a more tortuous or labryinth leakage path and, thus, acts to reduce leaks and to increase the effective pressure in the core.

Figure 4:
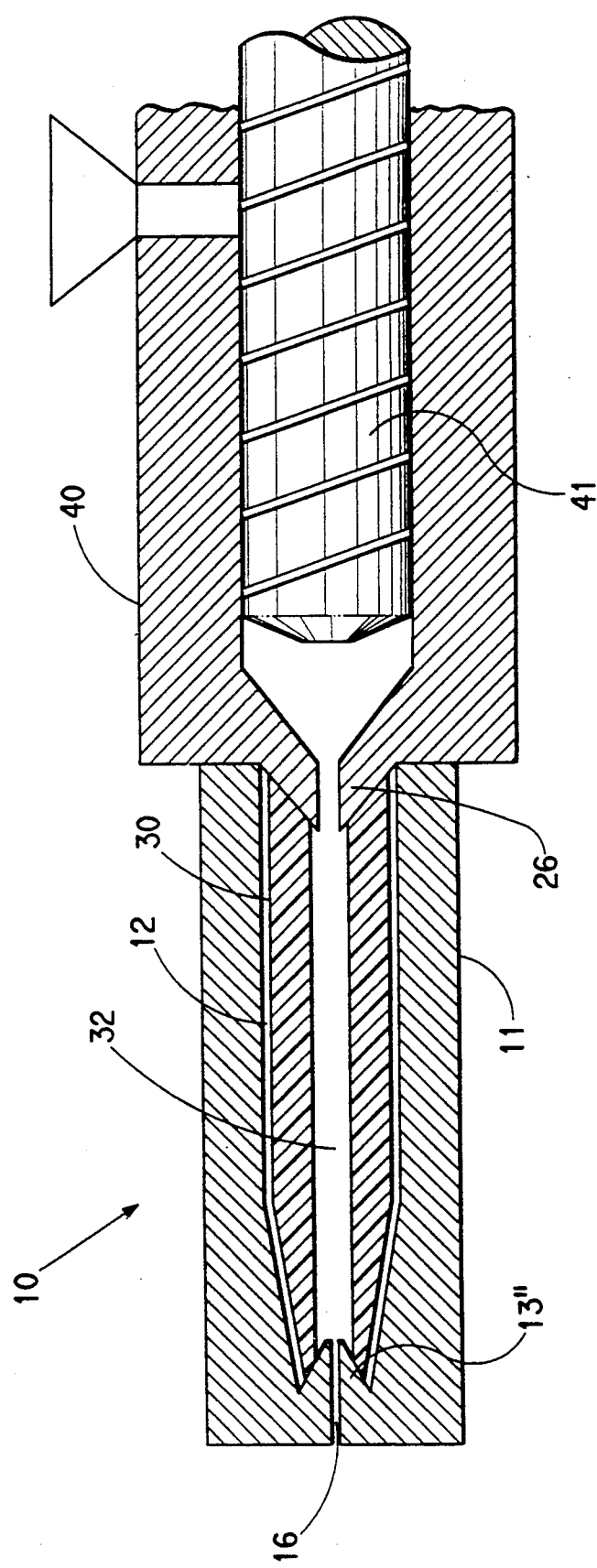
FIG. 4 is a cross-sectional view of a net shape molding system according to the present invention in which the core polymer is delivered and pressurized by an injection molding machine.

A more automated version of the process as shown in FIG. 4 uses a screw injection molding machine 40 in place of the actuator driven piston. In this case the core 32 of preform 30 is not prefilled with polymer but is instead filled by pumping from the molding machine effected by rotation of the plasticating screw 41 through the aperture in outlet 26 until melt appears at the bleed port 16 incorporated in end plug 13". At this point the bleed is closed and the cavity is pressurized by the action of the molding machine 40 typically accomplished by axial motion of screw 41.

Figure 5:
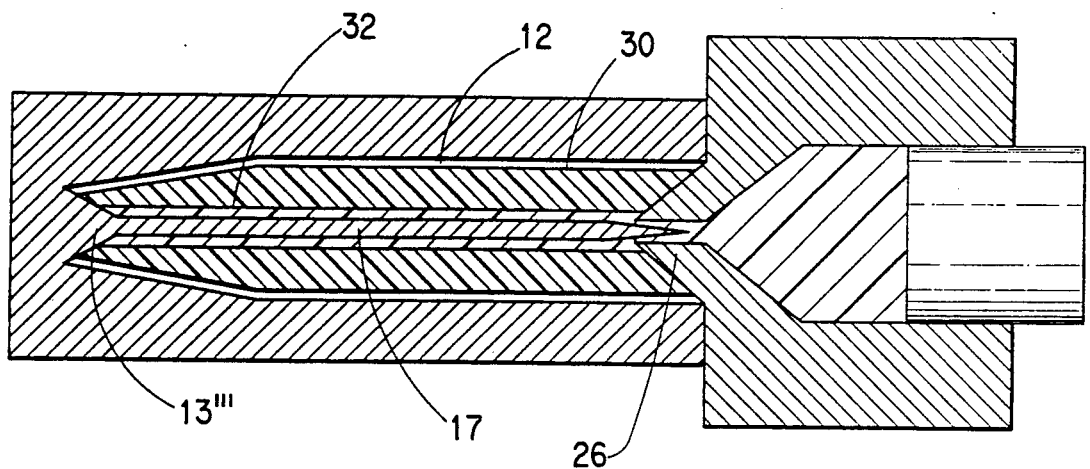
FIG. 5 is a cross-sectional view of a net shape molding system according to the present invention configured to produce a hollow finished part.

Note that as described up to this point, the process fills the core of the part with polymer; i.e. a solid finished structure is produced. This is desirable in many applications but may not be in others. FIG. 5 shows a mold configuration which maintains a hollow core in the finished part. End plug 13''' now incorporates a mandrel 17 which extends along mold cavity 12 and ends just inside the aperture in polymer outlet 26. Mandrel 17 may vary in diameter along its length but is always smaller than the diameter of core 32 of preform 30. In operation, the annulus formed between mandrel 17 and the core 32 is filled with polymer instead of the entire core 32. After consolidation and removal of mandrel 17, the finished part retains a hollow core.

Figure 6:
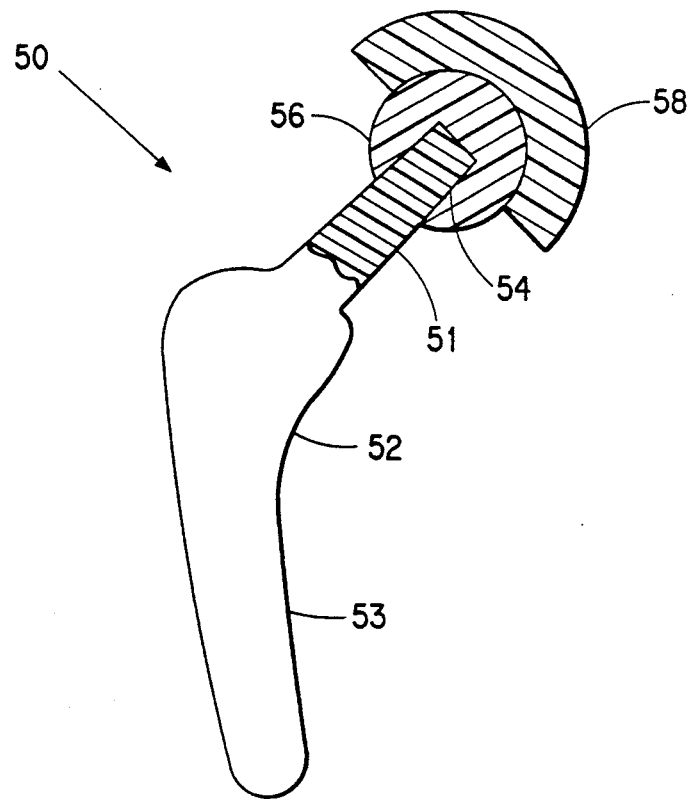
FIG. 6 is a partial cross-sectional view of a hip implant.

The present invention is not limited to the simple preform and mold cavity shapes shown in FIGS. 1 through 5 which were used for illustrative purposes Orthopedic devices may be prepared by the methods disclosed herein. A particular type of a more complex shape which can be molded by use of the present invention is the femoral stem component of a hip implant used in orthopedic surgery for the treatment of diseased or damaged human hip joints. The basic components of a hip implant are illustrated in FIG. 6, and generally depicted at 50. A neck 51 is secured to a proximal body which in turn is attached to a distal stem 53. The neck 51 engages a ball 56, which is rotatably enagaged in an artificial acetabular cup 58. Often the neck, proximal body and distal stem are fabricated as a single unitized component. Neck 51 includes a taper 54 which secures the unitized component to the ball 56.

Figure 7:
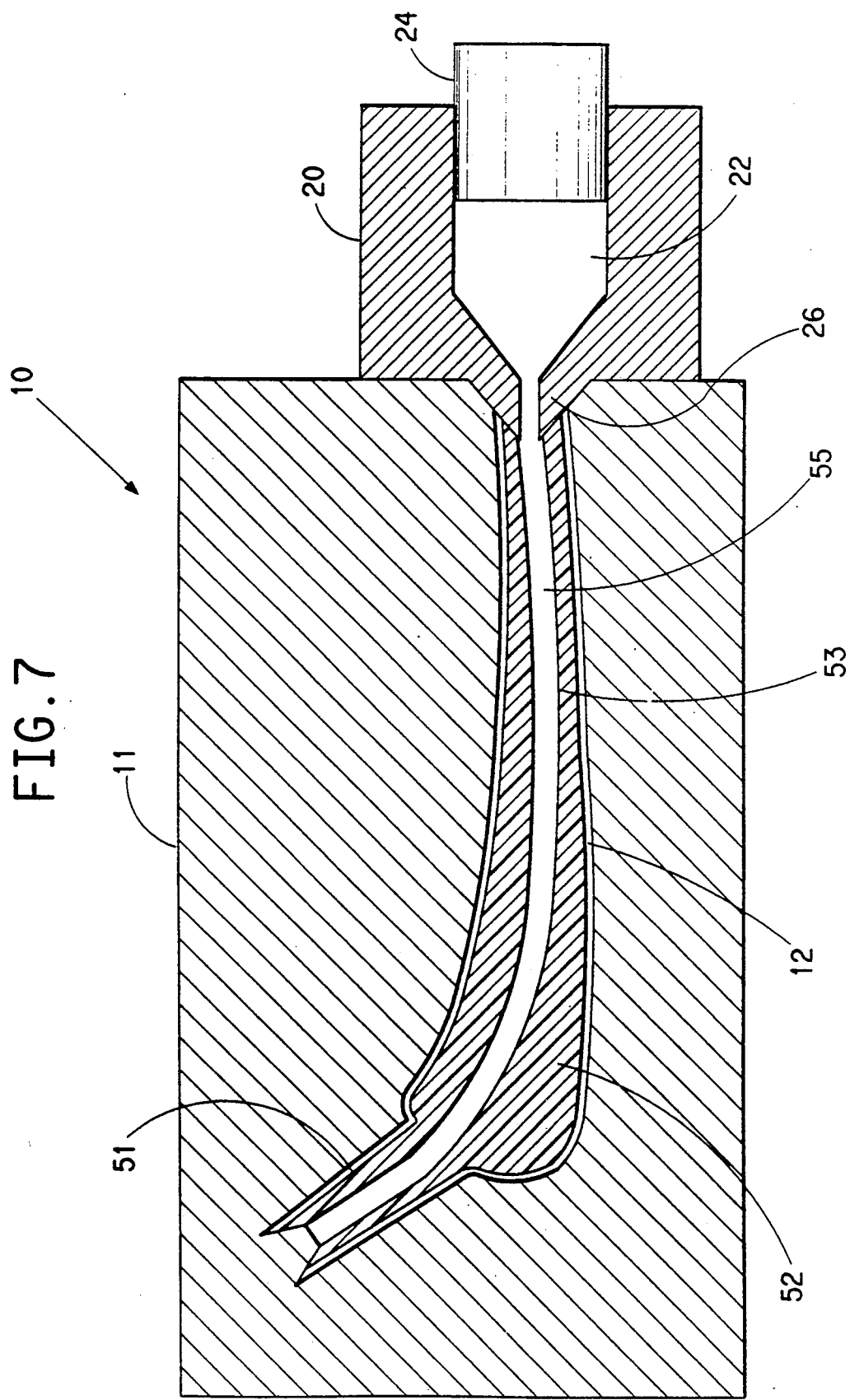
FIG. 7 is a cross-sectional view of a net shape molding system according to the present invention configured to produce a unitized neck, proximal body and distal stem for use in a hip implant system.

FIG. 7 depicts a molding system according to the present invention configured to consolidate a preform having the combined shape of the neck 51, proximal body 52 and distal stem 53 of a hip implant. As before, this unitized preform can be made by first impregnating reinforcing fiber bundles (preferably carbon, graphite, glass, or ceramic fiber) with a thermoplastic matrix polymer and then generating the preform shape using a filament winder, such as those made by the McClean Anderson Co., or a braiding machine, such as those made by the Wardwell Co. Especially useful for generating complex preforms of this type are fiber placement machines incorporating a robot such as that described in U.S. Pat. No. 4,750,960. In all cases these preform generating machines may incorporate means to apply heat and pressure to the preimpregnated tow so as to at least partially consolidate the preform. The hollow core 55 of the preform would again be prefilled with polymer and the consolidation process completed as described previously.

Figure 8:
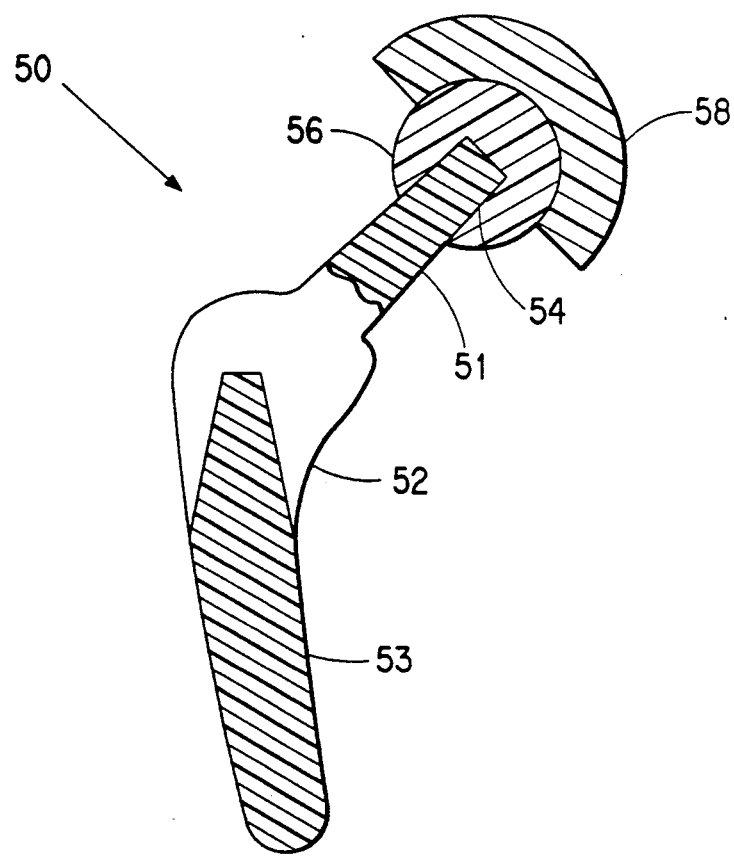
FIG. 8 is a cross-sectional view of another hip implant with a distal stem not unitized with the proximal body.

FIG. 8 shows another hip implant structure having a distal stem 53 which is not unitized to body 52. In particular, stem 53 may comprise an advanced composite material while neck 51 and body 52 are fabricated from metal. It is apparent that stem 53 can be made by a configuration of the present invention as depicted in FIGS. 2a, 2b 3 or 4.

Figure 9:
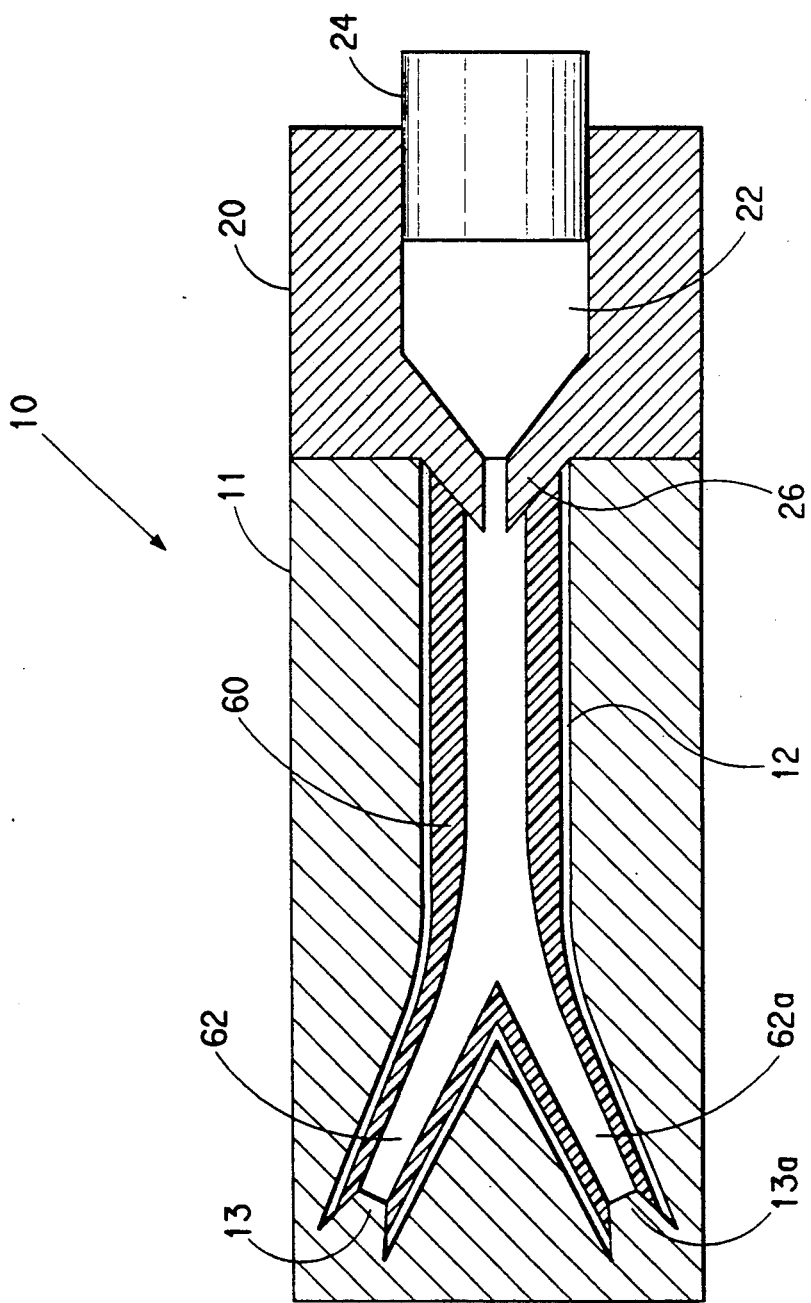
FIG. 9 is a cross-section view of a net shape molding system according to the present invention configured to mold a composite structure with a bifurcation.

FIG. 9 shows still another embodiment of the present invention in which a preform 60 with a bifurcation is molded. In order to insure proper consolidation of the two parts of the bifurcation, the preform 60 comprises two cores 62 and 62a and the mold comprises two tapered end plugs 13 and 13a. In addition molds can be configured with multiple polymer pressurization units to consolidate even more complex parts.

It is apparent that molds according to the present invention configured to produce complex parts may of necessity be made in two or more segments such that the segments are bolted or clamped together during processing but may be disassembled after cooling and depressurization to facilitate part removal.

The invention will be further understood and appreciated by having reference to the following examples.

EXAMPLES Example 1

A preform suitable for molding was produced from tow containing graphite filaments in a polysulfone polymer matrix. The preform was produced on a McClean-Anderson W60 winder utilizing a nonlinear winding program and equipped to apply heat and pressure during winding to at least partially consolidate the preform. The preform resembled the distal stem configuration 53 shown in FIG. 8 The ends of the preform were machined to allow it's installation in the molding system. That is, one end was machined to enable the hollow core of the preform to frictionally accomodate the tapered end plug of the mold and the other end was machined to frictionally accomodate the polymer outlet from the polymer pressurization unit. However, the outer surfaces of the preform were left in the as-wound condition.

Polysulfone inserts were machined to fit the core of the preform and the reservoir of the polymer pressurization unit. The preform was inserted in the mold; a gap of no larger than 0.05" existed between the exterior contour of the preform and the interior wall of the mold cavity. The system was heated to 360° C., using electrical heaters inserted in cavities installed in the mold body, while maintaining a load on the pressurization unit piston such that 200 pounds per square inch pressure was transmitted to the core of the preform. When the system reached 360° .C, the piston load was increased to give a 1000 pounds per square inch pressure in the core of the preform. The temperature and pressure was held for 10 minutes at which time the mold was rapidly quenched by introducing cooling water into passages machined into the mold body. After cooling, the mold was opened and finished part removed.

The effect of the process on the part was dramatic. The gap between the mold and the part had been eliminated and the surface of the part had achieved a smoothness matching that of the mold cavity; and equal to that of a machine ground finish Microscopy on polished cross-sections of the molded part shows that small scale porosity was significantly reduced by the process.

Example 2

This example illustrates the versatility of the invention in producing composite structures for a variety of applications. In this case the finished part is used as a thermowell to be installed, for example, in a reactor vessel containing extremely corrosive materials such as hydrochloric, sulfuric or phosphoric acids. In service, the thermowell contains a temperature measuring device such as a thermocouple and shields it from the harsh environment. The composite structure comprises graphite fiber reinforced fluoropolymers which have superior corrosion resistance and mechanical performance, including strength-to-weight and stiffness-to-weight, in comparison with incumbent metals such as titanium alloys or tantalum. By proper selection of the graphite reinforcement, the composite thermowell can exhibit acceptable thermal conductivity as required in this application.

Figure 10:
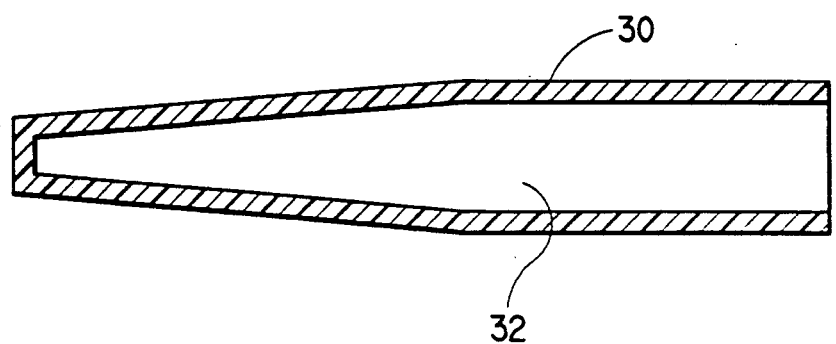
FIG. 10 is a cross-section view of a composite thermowell produced according to the present invention.

Preforms were produced from tow comprising graphite filaments preimpregnated with a fluoropolymer (either a copolymer of tetrafluoroethylene and perfluorovinylether such as Du Pont PFA 350 TM or a copolymer of tetrafluoroethylene and ethylene such as Du Pont TEFZEL TM ). The preform was fabricated by filament winding on a McClean Anderson W35 winder using a nonlinear winding program. The winder was equipped with devices to apply heat and pressure during winding to at least partially consolidate the preform. The preform resembled that shown in FIG. 2a. FIG. 10 depicts the geometry of the actual finished part, including a preform 30 with a core 32.

Inserts machined to fit the core of the preform and the reservoir of the polymer pressurization unit were produced from either PFA 350 TM or TEFZEL ethylene/tetrafluoroethylene copolymer Tefzel TM bar stock. The preform was inserted in the mold cavity; a gap of no larger than 0.05" existed between the exterior contour of the preform and interior wall of the mold cavity. The system was heated either to 390° C. for the PFA 350 TM tetrafluoroethylene copolymer preforms or 320° C. for the TEFZEL ethylene/tetrafluoroethylene copolymer Tefzel TM preforms using electrical heaters inserted in cavities installed in the mold body, while maintaining a load on the pressurization unit piston such that 600 pounds per square inch pressure was transmitted to the core of the preform. When the system reached the operating temperature, the piston load was increased to give a pressure of 4000 or 7000 pounds per square inch in the core of the preform. The temperature and pressure were held for a period of 30 minutes at which time the mold was rapidly quenched by introducing cooling water into passages machined into the mold body. Load was maintained on the piston during the cooling process to give a pressure of 4000 or 7000 pounds per square inch in the core of the preform. After cooling, the mold was opened and the finished part removed. As molded, the finished part has a solid core which must be removed by drilling or boring to produce the desired central aperture 32 shown in FIG. 10. A more preferable process for this part would incorporate the central mandrel 17 shown in FIG. 5, the mandrel shape selected to follow the dimensions of the inner bore of the finished part of FIG. 10.

Microscopic evaluation of cross-sections of the parts produced in this example shows the process effective in eliminating small scale voids of one to several fiber diameters in size. Consolidation improves as the process pressure is increased from 4000 to 7000 pounds per square inch in the core of the preform. In addition, the process produces a net shape outer surface needing little, if any, final machining.

It is readily appreciated by those skilled in the art that modifications can be made to the process of the present invention without departing from the spirit and scope thereof.

What is claimed is:

1. A method of making a composite structure comprising:
   providing a preform for disposition within a mold cavity, said preform having a hollow core portion and further having an external configuration which is undersized relative to the cavity of the mold;
   introducing said preform into said cavity having an internal configuration appropriate to the configuration of a finished part;
   plugging one or more openings to the core of said preform with one or more plugs to prevent polymer flow from these openings;
   introducing polymer into the core of the preform;
   heating the preform together with the polymer in the core so as to melt the polymer in the preform in the core;
   applying pressure to the polymer in the core of the preform via one or more remaining unplugged openings to the core of the preform to cause expansion of the preform against the internal configuration of the mold cavity and to consolidate the preform to form a finished part;
   cooling the finished part while maintaining pressure on the core; and
   removing the finished part from the mold.

2. The method of claim 1 further comprising heating the part and applying pressure to the core for a period sufficient to substantially eliminate the presence of voids in the finished part.

3. The method of claim 1 wherein the mold includes a polymer reservoir sized to contain polymer in excess of that within the core of the preform prior to pressurization and further shaped to urge polymer into the core while applying pressure to the core.

4. The method of claim 1 wherein the mold is attached to a screw injection molding machine which fills the core of the preform with polymer and also applies pressure to the core.

5. The method of claim 1 wherein the plugs are fixed to prevent polymer flow from the plugged openings.

6. The method of claim 1 wherein the plugs are moveable and have a load applied to them by of a spring or other actuator to impede polymer leakage through the plugged openings.

7. The method of claim 1 wherein one or more openings to the core are sealed to the mold by incorporation of threaded shapes into the plugs and the plugged openings.

8. The method of claim 1 wherein the plugged openings include bleed ports.

9. The method of claim 1 wherein the one or more plugs has a removable mandrel attached thereto spanning the length of the mold cavity such that the finished part has a hollow core.

10. A method of making a composite structure comprising:
    providing a thermoplastic matrix, fiber reinforced preform for disposition within a mold cavity, said preform having a hollow core portion and further having an external configuration which is undersized relative to the cavity of the mold;
    introducing said preform into said cavity having an internal configuration appropriate to the configuration of a finished part;
    plugging one or more openings to the core of said preform with one or more plugs to prevent polymer flow from these openings;
    introducing polymer into the preform;
    heating the preform together with the polymer in the core so as to melt the polymer the preform in the core;
    applying pressure to the polymer in the core of the preform via one or more remaining, unplugged openings to the core of the preform to cause expansion of the preform against the internal configuration of the mold cavity and to consolidate the preform to form a finished part;
    cooling the finished part while maintaining pressure on the core; and
    removing the finished part from the mold.

11. The method of claim 10 wherein the fibers are selected from the group consisting of carbon, glass and aramid fiber.

12. The method of claim 10 wherein the thermoplastic matrix is selected from the group consisting of polyamide, polyester, polysulfone, polyether-ether-ketone, polyether-ketone-ketone, polyimide, copolymers of tetrafluoroethylene and perfluorovinylether and copolymers of polytetrafluoroethylene and ethylene.

13. The method of claim 10 wherein the polymer introduced into the core is selected from the group consisting of polyamide, polyester, polysulfone, polyether-ether-ketone, polyether-ketone-ketone, polyimide, copolymers of tetrafluoroethylene and perfluorovinylether and copolymers of polytetrafluoroethylene and ethylene.

14. The method of claim 10 wherein the preform is made by filament winding.

15. The method of claim 10 wherein the preform is made by braiding.

16. The method of claim 10 wherein the preform is made by fiber placement machines incorporating a robot,

* * * * *

UNITED STATES PATENT AND TRADEMARK OFFICE
CERTIFICATE OF CORRECTION

PATENT NO. : 5,198,173
DATED : March 30, 1993
INVENTOR(S) : Albert Terzian et al It is certified that error appears in the above-identified patent and that said Letters Patent is hereby corrected as shown below:

Column 9, line 25, change "in the preform in" to
-- in the preform and in --.

Column 9, line 54, change "to them by of" to
-- to them by --.

Column 10, line 24, change "the polymer the preform in" to
-- the polymer in the preform and in --.

Signed and Sealed this

Ninth Day of May, 1995

BRUCE LEHMAN

Attest:

Attesting Officer

Commissioner of Patents and Trademarks